(12) United States Patent
Acton

(10) Patent No.: US 9,629,976 B1
(45) Date of Patent: Apr. 25, 2017

(54) METHODS FOR INDEPENDENT ENTRAINMENT OF VISUAL FIELD ZONES

(71) Applicant: George Acton, Shreveport, LA (US)

(72) Inventor: George Acton, Shreveport, LA (US)

(*) Notice: Subject to any disclaimer, the term of this patent is extended or adjusted under 35 U.S.C. 154(b) by 601 days.

(21) Appl. No.: 14/138,376

(22) Filed: Dec. 23, 2013

(51) Int. Cl.
| | |
|---|---|
| *A61M 21/02* | (2006.01) |
| *A61B 5/00* | (2006.01) |
| *A61B 5/024* | (2006.01) |
| *A61B 5/0476* | (2006.01) |
| *A61B 5/08* | (2006.01) |
| *A61H 5/00* | (2006.01) |
| *A61M 21/00* | (2006.01) |

(52) U.S. Cl.
CPC .............. *A61M 21/02* (2013.01); *A61B 5/024* (2013.01); *A61B 5/0476* (2013.01); *A61B 5/0816* (2013.01); *A61B 5/486* (2013.01); *A61B 5/4836* (2013.01); *A61H 5/00* (2013.01); *A61M 2021/0044* (2013.01)

(58) Field of Classification Search
CPC ................. A61M 21/00; A61M 21/02; A61M 2021/0005; A61M 2021/0044; A61M 2021/005; A61N 5/06; A61N 5/0613; A61N 5/0618; A61N 5/0622
See application file for complete search history.

(56) References Cited

U.S. PATENT DOCUMENTS

| | | | | |
|---|---|---|---|---|
| 3,822,693 | A * | 7/1974 | King ................... | A61M 21/00 351/239 |
| 5,709,645 | A * | 1/1998 | Siever ................. | A61M 21/00 600/26 |
| 2009/0156886 | A1* | 6/2009 | Burgio ................. | A61B 5/224 600/27 |
| 2012/0123191 | A1* | 5/2012 | Surenthiran ........... | A61H 5/00 600/27 |

* cited by examiner

*Primary Examiner* — Charles A Marmor, II
*Assistant Examiner* — Carrie R Dorna
(74) *Attorney, Agent, or Firm* — David P. Lentini

(57) ABSTRACT

An entrainment method for stimulation of a visual field in a subject includes presenting a visual stimulation field to a subject, the visual stimulation field disposed at a distance of at least about 6 inches from the subject; and flashing at least one zone of the visual stimulation field for a selected duration and at a selected flash frequency.

19 Claims, 6 Drawing Sheets

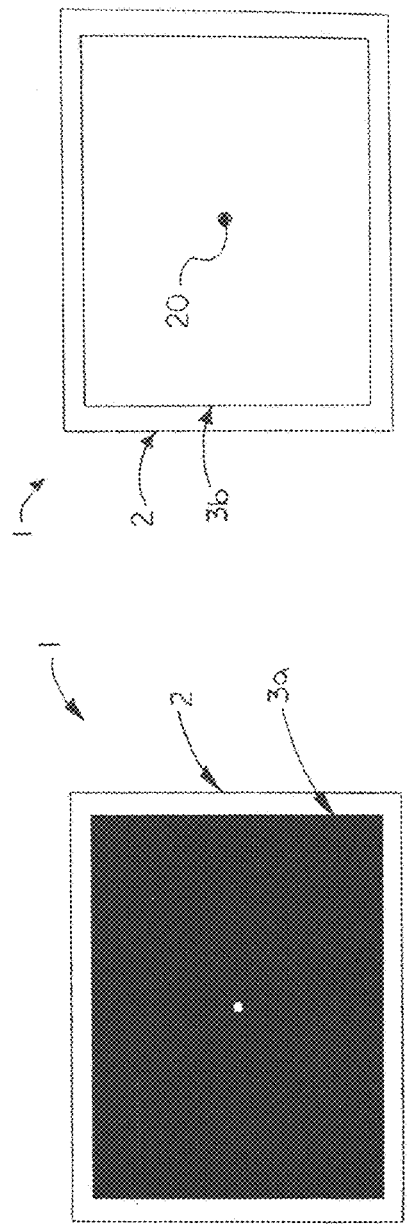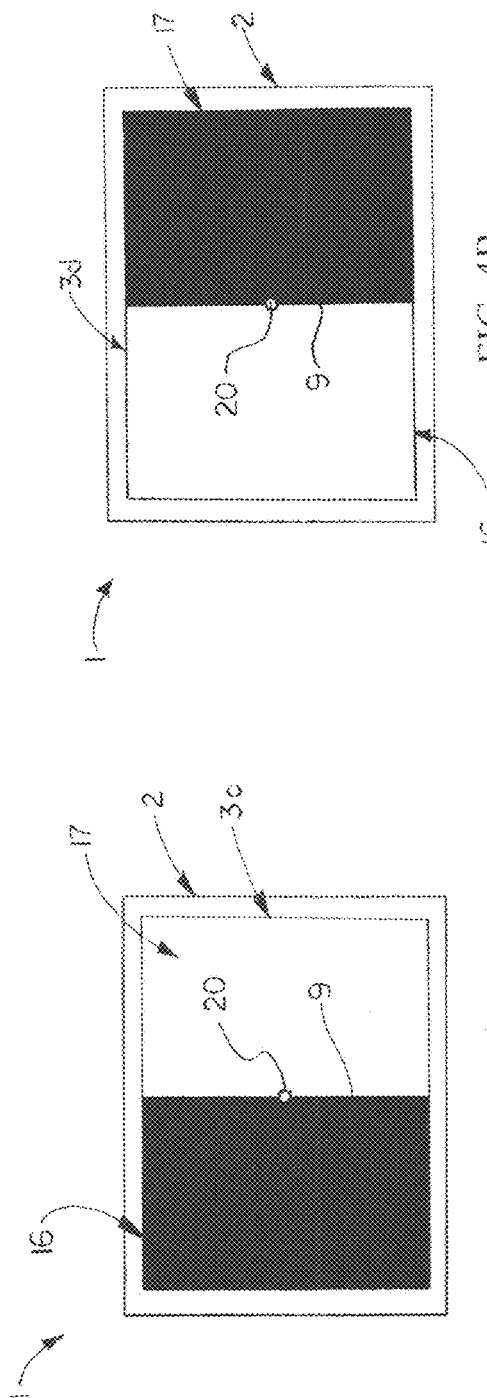

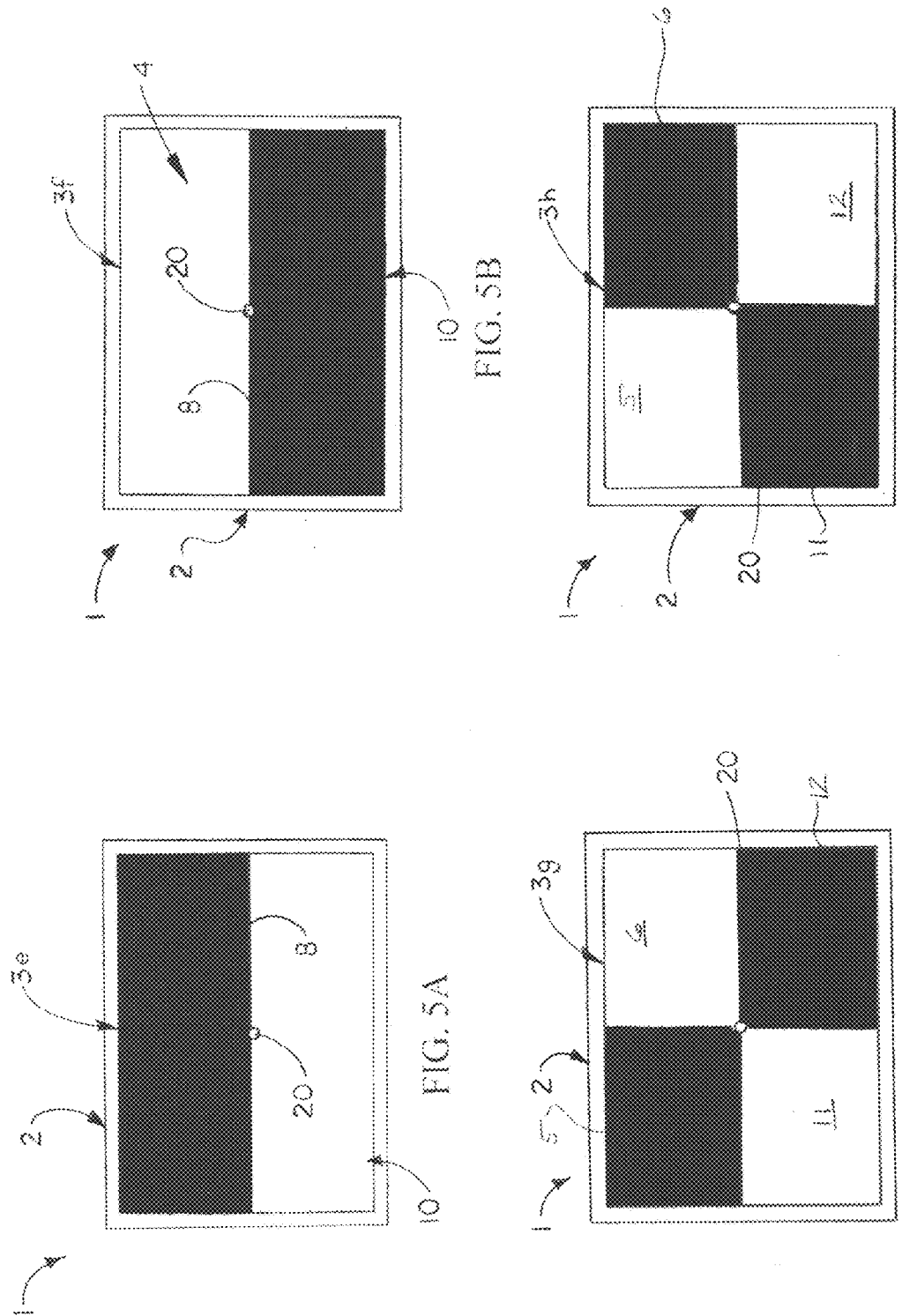

METHODS FOR INDEPENDENT ENTRAINMENT OF VISUAL FIELD ZONES

CROSS-REFERENCE TO RELATED APPLICATIONS

This application claims the benefit of U.S. provisional application No. 61/740,634, filed Dec. 21, 2012 and entitled INDEPENDENT STIMULATION OF VISUAL FIELD ZONES, and is related to U.S. application Ser. No. 13/784,193, filed Mar. 4, 2013 and entitled METHODS FOR TREATING BRAIN MALFUNCTIONS, which provisional application and related application are incorporated by reference herein in their entireties.

FIELD

Illustrative embodiments of the disclosure generally relate to methods for modifying the electrical neural activity of the human brain. More particularly, illustrative embodiments of the disclosure relate to entrainment methods for independent stimulation of a visual field in a subject, in which methods photic stimuli are presented to different areas of a subject's visual field to selectively stimulate or inhibit neurological activity in various parts of the subject's central nervous system and potentially treat various brain malfunctions.

BACKGROUND

The background description provided herein is solely for the purpose of generally presenting the context of the illustrative embodiments of the disclosure. Aspects of the background description are neither expressly nor impliedly admitted as prior art against the claimed subject matter.

The invention brings together findings from two areas of neuroscience: (1) functional specializations of different zones of the retina and its connections, and (2) entrainment of rhythmic processes in the nervous system by stimuli of constant frequency (entrainment).

Specializations of the left and right hemispheres have long been recognized, with the dominant hemisphere (the left in most righthanded individuals) predominant in language. rule-based and routine behavior, while the nondominant hemisphere predominates in spatial relations, context-dependent behavior and responses to novelty. The nondominant hemisphere is also better at low spatial frequency or global and coordinating spatial processing, while the dominant hemisphere is better at high spatial frequency or local and categorical spatial processing.

Altering the balance of activity between the hemispheres could be useful in treatment of mood and anxiety states. Depression has been shown to involve increased activity in portions of the nondominant hemisphere. Individuals with posttraumatic stress disorder (PTSD) often have a lesser degree off specialization between the hemispheres, and this has been attributed to less suppression by the dominant hemisphere of brain structures for registering anxiety, such as the amygdaloid nucleus.

The retina has a central visual field zone in which light-sensitive rod cells and neurons are tightly packed in a small central zone (the fovea) and a peripheral visual field zone in which mostly rod cells exhibit higher sensitivity in dim light. Approximately 50% of the nerve fibers in the optic nerve originate in the fovea. which comprises only the central 2 degrees of the visual field. From the visual sensory areas of the cerebral cortex, a pathway runs to a motor area for controlling eye movements (saccades). Altering the balance of attention between central and peripheral zones would be expected to affect focus on an task versus interruption by distractions.

The upper visual field zone receives information about distant space, whereas the lower visual field zone receives information about close space that is subject to manual manipulation. The neural connections of the upper visual field zone and the lower visual field zone reflect these functional differences, with a pathway from the upper visual field zone connecting to processing areas near those for memory and emotion and a pathway from the lower visual field zone connecting to an area near the motor centers for hand movement and body orientation. Asymmetries in favor of the lower visual field zone have been demonstrated for temporal and Contrast sensitivities, visual acuity, spatial resolution, orientation, hue and motion processing. In contrast. the upper visual field zone advantages have been demonstrated in visual search, apparent size and object recognition tasks. One summarization is that the lower visual field zone is concerned with "where", while the upper visual field zone is concerned with "what".

Altering the balance of activity in favor of the lower visual zone would be expected to bias the subjects behavior toward immediate motor activity and consummatory behavior such as eating. Emphasizing the upper zone would shift the balance towards observing and orienting to a situation before taking action, drawing on memory of previous events, and impulse control.

Neural systems for memory are an important connection of the upper visual field, and these areas of the brain are the first and most severely affected in Alzheimer's disease. This raises the question of whether the progression of the disease might be slowed by inhibiting activity in these areas via selective entrainment. Decreased activity would be expected to slow the production of beta amyloid, thought to be toxic for neurons at high levels. General inhibition of neural activity has been suggested as beneficial in Alzheimer's, but selective inhibition might have advantages.

Electroencephalogram (EEG) measurement of the human brain reveals periodic neural activity whose frequencies as associated with different mental states. Delta waves have a frequency of less than 5 Hz and occur in deep sleep. Theta waves (5-7 Hz) accompany sleep onset and unusual mental states such as waking dreams. Alpha waves (8-12 Hz) accompany an awake and alert but unfocused mental state. Beta waves (13-30 Hz) accompany selective attention to external stimuli or internal thoughts. Gamma waves (30+ Hz) accompany more intense and focused mental activity.

The lower EEG frequencies are generally associated with activity in larger areas of the cerebral cortex, with increased amplitude. For example, delta waves sweep across large regions of the cerebral cortex in deep stages of sleep. Alpha waves occur during waking and involve wide areas of the cerebral cortex. Beta waves are thought to reflect activity in extended networks of neurons involving connections between widely separated parts of the brain. Gamma activity is produced by small local networks.

A feature of alpha and theta rhythms is that they can be generated by pacemaker neurons in the thalamus, which project to specific regions of the cortex. Activity at those frequencies can spread within and between the thalamus and cortex. Practitioners of meditation have exhibited widespread synchronized alpha and theta activity involving large areas of cortex.

Alpha rhythms appear over the visual cortex when the eyes are closed and in other situations in which a region of the cerebral cortex is inactive. Thus, the alpha rhythm is believed to characterize the "idle mode" of the brain, as it is associated with inhibition of cortical activity and increased threshold for sensory stimulation.

When a repetitive stimulus is presented to a subject, the electrical activity of the brain settles into waves of the same frequency in a process known as entrainment. It is known that stimulation in the alpha range, or lower, inhibits neural activity and decreases metabolism, and conversely stimulation at higher frequencies increases activity. This offers the possibility of stimulating one zone of the visual field and simultaneously inhibiting another, enhancing the effectiveness of the entrainment in modulating brain activity.

Entrainment with a light source close to the eye is effective, but has poor specificity for single zones of the visual field. The effect is blurry because the eyes optical system cannot achieve a sharp focus. And because there are no cues for stabilizing the visual axis, the focus tends to wander, and directing the stimulus to a sharply defined zone is problematic. The system of the present invention overcomes both these drawbacks by presenting the image at a distance sufficient to allow for sharp focus (about six inches) and instructing the subject to keep the eyes open and maintain attention on a small area of the image, possibly with a visual marker to direct the gaze. Variations include moving the indicator dot and zones of stimulation in tandem, which would have the effect of maintaining constant zones of stimulation on the retina. Another possibility is having the subject view a picture or text occupying part of the screen while presenting entraining stimuli. This would make the retinal stimulation less precise, but accurate enough for a useful entrainment effect.

There are many potential therapeutic applications of the technique of the invention. Of special interest are the cases of attention deficit disorder (ADD), post-traumatic stress disorder (PTSD) and Alzheimer's Disease. ADD is thought to involve inappropriate occurrence of alpha rhythm interrupting the beta rhythm associated with a cognitive task. Entrainment to suppress this alpha rhythm might be helpful. PTSD patients as a group have decreased relative activity of the dominant hemisphere (the left in right-handers), and this is thought to reflect weaker executive function in suppressing brain structures for anxiety and fear (the amygdaloid nuclei). Changing the balance of activity between the hemispheres may be of benefit. In Alzheimer's Disease, areas subserving memory are most vulnerable, and selective lowering of metabolic activity in these pathways may delay accumulation of the toxic compound beta amyloid, which builds up as a by-product of neural activity.

A common feature of these interventions is that simultaneous enhancement and inhibition of activity in different brain areas may be advantageous, and this is achievable with the invention's approach of selective zonal stimulation.

SUMMARY

Illustrative embodiments of the disclosure are generally directed to an entrainment method for stimulation of a visual field in a subject. An illustrative embodiment of the method includes presenting a visual stimulation field to a subject, the visual stimulation field disposed at a distance of at least about 6 inches from the subject; and flashing at least one zone of the visual stimulation field for a selected duration and at a selected flash frequency.

BRIEF DESCRIPTION OF THE DRAWINGS

Illustrative embodiments of the disclosure will now be described, by way of example, with reference to the accompanying drawings, in which:

FIGS. 3A and 3B are respective front views of a display screen with a flashing whole screen visual stimulation field in an exemplary central-peripheral application of an illustrative embodiment of the methods for independent stimulation of a visual field in a subject;

FIGS. 4A and 4B are respective front views of a display screen with flashing left and right hemi-field zones in a visual stimulation field according to an exemplary left-right application of an illustrative embodiment of the methods for independent stimulation of a visual field in a subject;

FIGS. 5A and 5B are respective front views of a display screen with flashing upper and lower hemi-field zones in a visual stimulation field according to an exemplary upper-lower application of an illustrative embodiment of the methods for independent stimulation of a visual field in a subject;

FIGS. 6A and 6B are respective front views of a display screen with flashing quadrant zones in a visual stimulation field according to an illustrative embodiment of the methods for independent stimulation of a visual field in a subject;

DETAILED DESCRIPTION

Figure 1:
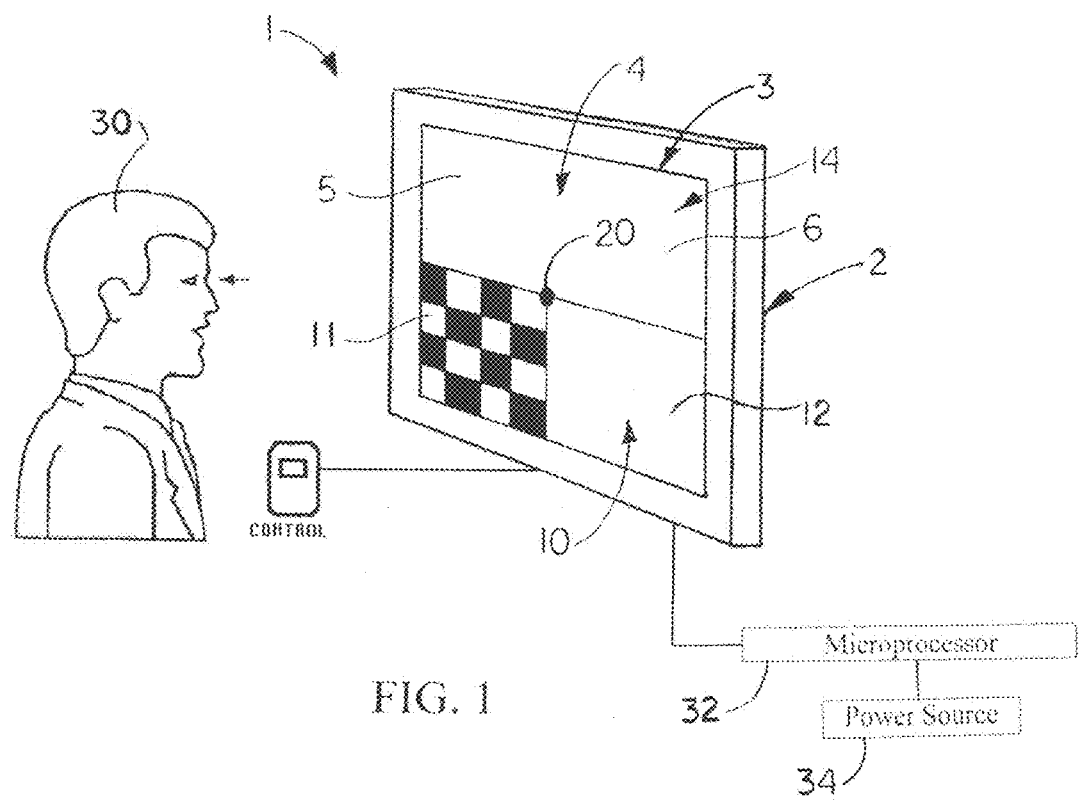
FIG. 1 is a perspective view of an exemplary visual field stimulation system which is suitable for implementation of an illustrative embodiment of the methods for independent stimulation of a visual field in a subject, in exemplary implementation of the methods.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Illustrative embodiments of the disclosure are generally directed to entrainment methods for independent stimulation of a visual field in a subject in which photic stimuli are presented to different parts of a subject's visual field to stimulate or inhibit neurological activity in various parts of the subject's central nervous system in the treatment of various brain malfunctions. Entrainment is a process in which the electrical activity of the brain settles into brainwaves of the same frequency when a repetitive stimulus is presented to a subject. Brainwave frequencies which are induced by entrainment may spread from the area which is stimulated to involve other parts of the cortex.

In some exemplary applications, the methods may be useful for treating brain malfunctions which are caused or exacerbated by excessive levels of beta amyloid protein (Ab) in neural tissues. Accordingly, the methods may include lowering the EEG (electroencephalogram) frequency of brainwaves which characterize the waking state to reduce neural activity and metabolism. Reduction of neural activity and metabolism may, in turn, lower the rate of production of Ab in neural tissues and prevent or reduce formation of amyloid plaques in the brain, halting or at least slowing progression of the brain malfunction. Non-limiting examples of brain malfunctions which can be treated using the methods include Alzheimer's Disease, Down Syndrome and Fragile X Syndrome. In other exemplary applications, the methods may be useful for treating anxiety such as PTSD (Post Traumatic Stress Disorder) or ADD (Attention Deficit Disorder), for example and without limitation. The stimulation of visual field zones according to the entrainment methods may be implemented alone or in combination with at least one non-visual stimulus such as non-visual stimulus selected from the group consisting of auditory stimulus (isochronic tones, binaural beats, music) tactile stimuli, kinesthetic stimuli, somatic electrical stimuli, transcranial electrical stimuli and transcranial magnetic stimuli or any combination thereof to the subject.

Binaural beats are perceived sounds produced within the nervous system. When pure tones of slightly different frequencies are presented separately to each ear, the subject experiences the sensation of a sound at the frequency representing the difference of the input frequencies. Binaural beats may have effects on the EEG frequency spectrum which may be beneficial in lowering Ab levels.

Neurofeedback involves monitoring a physiologic variable not under conscious control and signaling to the subject when the desired change is present, usually with an audible tone. It can be used with EEG frequencies, pulse rate, breathing rate, galvanic skin response, muscle tone, skin conductance, heart rate and pain perception. In some embodiments, the physiologic variable may be used to modify at least one parameter including but not limited to changes in frequency, color and intensity of at least one of the at least one zone of the visual stimulation field.

Some illustrative embodiments of the disclosure may include obtaining a subject diagnosed with a brain malfunction which is caused or exacerbated by excessive levels of beta amyloid protein. A stimulus protocol may be formulated. The stimulus protocol may include applying a visual stimulation field having flashing light of selected frequency to one or more areas or zones in the visual field of a subject. In some embodiments, the application of flashing light to the visual field of the subject may be applied to the eyes of the subject while the subject's eyes are open. Having the subject 30 view the visual stimulation field 3 on a computer monitor or other digital medium or device in an eyes-open condition may optimize targeting precision and visual detail. The flashing light may be applied to the eyes of the subject while having the subject view the visual stimulation field on a computer monitor, LED screen, cathode ray tube, computer tablet display, goggles, glasses or other optical device such as an optical apparatus adapted to present a focused image on a retina of the subject 30. The stimulus protocol may cause a reduction or increase in the EEG frequency of brainwaves specific to brain areas or regions in the subject. The reduction in the EEG frequency may cause a reduction in Ab production in the subject. The reduction in Ab production in the subject may result in a halting or at least slowing of the progression of the brain malfunction in the subject. The progress of the brain malfunction may be monitored throughout the treatment regimen.

In some embodiments, the stimulus protocol of the methods may include presentation of a visual stimulation field having one or more flashing visual stimulation field zones to the subject at a selected frequency and for a selected period of time. The flashing visual stimulation field zone or zones may stimulate one or more areas of the subject's retina and thereby activate or inhibit corresponding regions of the central nervous system. The color of the visual stimulation field or visual stimulation field zones may be selectable.

In some embodiments, the visual stimulation field which is selected for therapy may be a whole screen visual stimulation field zone which may encompass substantially the entire viewing area of the display screen. The whole screen visual stimulation field zone may flash at a selected frequency for a selected period of time. In some embodiments, the visual stimulation field zone may be divided into two or more flashing visual stimulation field zones such as an upper hemi-field zone and a lower hemi-field zone. The upper hemi-field zone and the lower hemi-field zone may occupy upper and lower halves, respectively, of the viewing area on the display screen. Another visual stimulation field zone may include a flashing left hemi-field zone and a flashing right hemi-field zone which may occupy left and right halves, respectively, of the viewing area on the display screen. Yet another visual stimulation field zone may include at least one flashing quadrant zone. The quadrant zones may include a flashing upper left quadrant zone, a flashing upper right quadrant zone, a flashing lower left quadrant zone and a flashing lower right quadrant zone. Still another visual stimulation field zone may include at least one quadrant zone which is subdivided into multiple flashing quadrant subdivision zones.

The subject may be disposed at a selected distance from the flashing whole screen visual stimulation field zone or the multiple flashing visual stimulation field zones. In some embodiments, the subject may be disposed at a distance of at least about 6 inches from the visual stimulation field zone or visual stimulation field zones. In some embodiments, a visual fixation point may appear at substantially the center of the whole screen visual stimulation field zone or the multiple visual stimulation field zones. The visual fixation point may be any of various sizes and may correspond to light of various intensities and/or colors. In some embodiments, the visual fixation point may include at least one dot. During implementation of the treatment protocol, both eyes of the subject may be fixed on the visual fixation point as the flashing visual stimulation field or visual stimulation field zones is/are presented to the subject. In some embodiments, the visual fixation point may move on the visual stimulation field while the visual simulation field or visual stimulation field zones are maintained in a static relative position, such that the visual stimulation field or visual stimulation field zones produce constant stimulation to zones of the retina of the subject.

Some illustrative embodiments of the disclosure may include obtaining a subject diagnosed with an anxiety disorder such as PTSD (Post Traumatic Stress Disorder) or ADD (Attention Deficit Disorder), for example and without limitation. A stimulus protocol may be formulated. The stimulus protocol may include applying a flashing whole screen visual stimulation field zone or multiple flashing visual stimulation field zones of selected frequency to one or more areas on the visual field of a subject. In some embodiments, the application of a flashing whole screen visual stimulation field zone or one or more flashing visual stimulation field zones to the area or areas on the visual field of the subject may be applied to the eyes of the subject while the eyes of the subject are open. The flashing whole screen visual stimulation field zone or visual stimulation field zones may be applied to the eyes of the subject while having the subject view the visual stimulation field zone or visual stimulation field zones on a computer monitor. The stimulus protocol may cause a reduction in the EEG frequency of brainwaves in the subject. The reduction in the EEG frequency may cause abatement of the anxiety or attention deficit disorder. The progress of the brain malfunction may be monitored throughout the treatment regimen.

Figure 2:
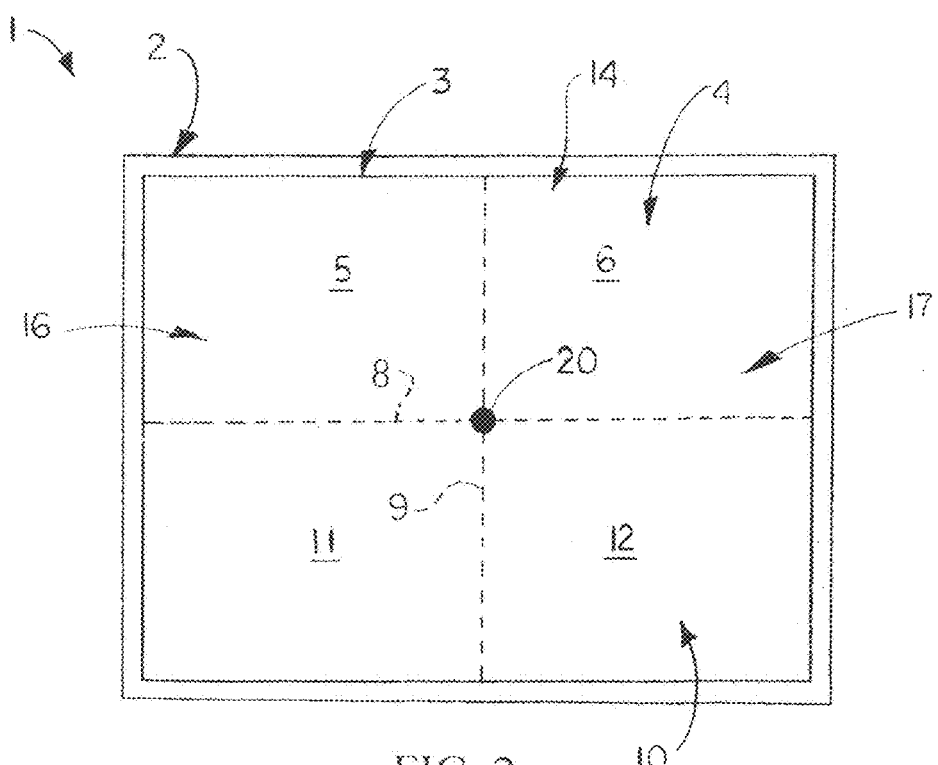
FIG. 2 is a front view of a display screen of an exemplary visual field stimulation system, with an exemplary visual stimulation field presented on the display screen in implementation of an illustrative embodiment of the methods for independent stimulation of a visual field in a subject.
Figure 2A:
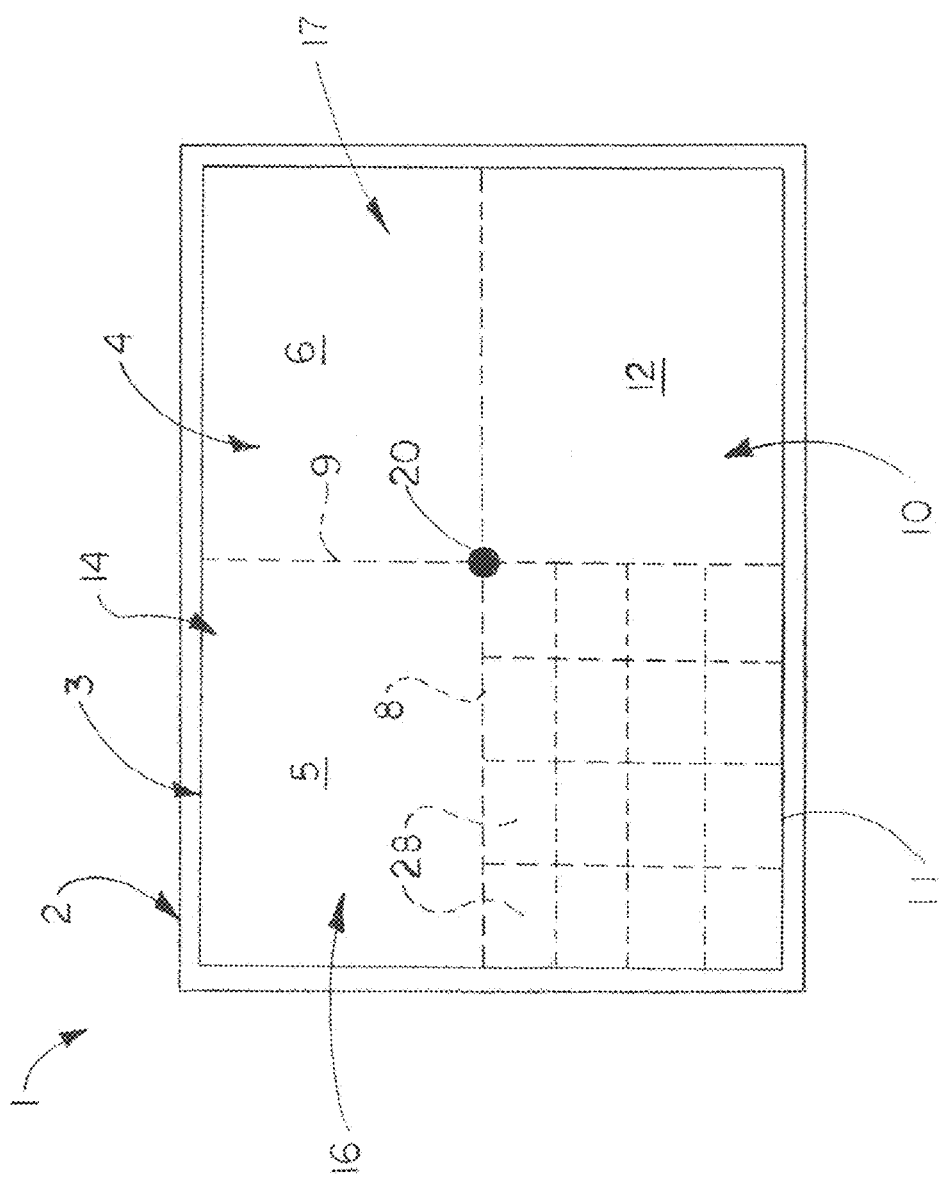
FIG. 2A is a front view of a display screen of an exemplary visual field stimulation system, with an alternative exemplary visual stimulation field presented on the display screen in implementation of an illustrative embodiment of the methods for independent stimulation of a visual field in a subject.

Referring to FIGS. 1, 2 and 2A of the drawings, an exemplary visual field stimulation system, hereinafter system, in implementation of the entrainment methods is generally indicated by reference numeral 1. The system 1 includes a display screen 2 which may be provided on a computer monitor, LED screen, cathode ray tube, computer tablet display, goggles, glasses or other optical device such as an optical apparatus adapted to present a focused image on a retina of the subject 30. Accordingly, as illustrated in FIG. 1, the display screen 2 interfaces with a microprocessor 32 and a power source 34. The microprocessor 32 is loaded with software which implements the methods. As further illustrated in FIG. 1, in implementation of the entrainment methods, at least one visual stimulation field zone 3 is presented on the display screen 2 to a subject 30 in the treatment of various brain malfunctions in the subject 30. As used herein, "visual stimulation field" includes but is not limited to any two-dimensional visual image with or without zones. In some applications of the methods, a flashing whole screen visual stimulation field zone 3 may encompass substantially the entire surface area of the display screen 2. In some applications, the whole screen visual stimulation field zone 3 may be divided into a pattern of multiple flashing visual stimulation field zones 14. The flashing whole screen visual stimulation field zone 3 or the pattern of flashing visual stimulation field zones 14 may stimulate or inhibit neurological activity in various parts of the central nervous system of the subject 30 in treatment of the brain malfunctions. The stimulated zones of the retina in the subject 30 correspond to respective areas of the whole screen visual stimulation field zone 3 or the respective visual stimulation field zones 14.

As illustrated in FIG. 2, in some applications, the visual stimulation field zones 14 may include a flashing upper hemi-field zone 4 and a flashing lower hemi-field zone 10, separated by a center horizontal visual stimulation field dividing line 8. Alternatively, some of the visual stimulation field zones 14 may include a flashing left hemi-field zone 16 and a flashing right hemi-field zone 17, separated by a center vertical visual stimulation field dividing line 9. Some of the visual stimulation field zones 14 may include at least one of a flashing upper left quadrant zone 5, a flashing upper right quadrant zone 6, a flashing lower left quadrant zone 11 and a flashing lower right quadrant zone 12. In some applications, a visual fixation point 20 may appear at substantially the center of the whole screen visual stimulation field zone 3. The visual fixation point 20 and the whole screen visual stimulation field zone 3 or visual stimulation field zones 14 may form a central field zone and a peripheral field zone, respectively. The subject 30 may be instructed to fix his or her visual focus on the visual fixation point 20 throughout at least a portion of the stimulus protocol. As illustrated in FIG. 2A, in some applications, at least one of the upper left quadrant zone 5, the upper right quadrant zone 6, the lower left quadrant zone 11 and the lower right quadrant zone 12 may be subdivided into multiple flashing quadrant subdivision zones 28.

In some embodiments, the color of the flashing whole screen visual stimulation field zone 3 or visual stimulation field zones 14 may be selectable for each stimulus protocol. Exemplary colors for the whole screen visual stimulation field 3 or visual stimulation field zones 14 include but are not limited to white, red, blue, yellow and green. In some embodiments, the size and color of the visual fixation point 20 may be selectable for each stimulus protocol. Since color perception is effectively confined to the central visual field, using a flashing colored whole screen visual stimulation field 3 or visual stimulation field zones 14 may assist the subject 30 in maintaining visual fixation and increase the likelihood that the stimuli reach the correct areas of the visual field. In some embodiments, the whole screen visual stimulation field zone 3 or visual stimulation field zones 14 may not be limited to a single color or black/white cycle but may include smaller patterns or fine details. In some embodiments, the whole screen visual stimulation field zone 3 or visual stimulation field zones 14 may have a visual content such as black, white, solid color, repeated pattern and picture with fine detail.

In some embodiments, the flash frequency of the whole screen visual stimulation field 3 or the visual stimulation field zones 14 may be selectable for each stimulus protocol. Selection of flash frequency can be used for differential activation and inhibition over different parts of the visual field, leading to corresponding effects on cortical areas of the subject 30. Exemplary flash frequencies which may be selected for the whole screen visual stimulation field zone 3 or the visual stimulation field zones 14 in each stimulus protocol may be generally from about 5 Hz to about 20 Hz. In some applications, exemplary flash frequencies which are selectable for the whole screen visual stimulation field zone 3 or the visual stimulation field zones 14 in each stimulus protocol may be in the range of about 15~20 Hz. In some applications, exemplary flash frequencies selectable for the visual stimulation field 3 or the visual stimulation field zones 14 in each stimulus protocol may be in the range of about 8~12 Hz to decrease nervous system activity. The flash frequencies of the visual stimulation field zones 14 may be independently selectable. For example and without limitation, in FIG. 2, some applications of the methods may include the flashing upper hemi-field zone 4 and the flashing lower hemi-field zone 10. The flash frequency of the upper hemi-field zone 4 and the flash frequency of the lower hemi-field zone 10 may be independently selectable. For example and without limitation, the flash frequency which is selected for the upper hemi-field zone 4 may be about 5 Hz, whereas the flash frequency which is selected for the lower hemi-field zone 10 may be about 15 Hz. Some applications of the methods may include a left hemi-field zone 16 and a right hemi-field zone 17 with independently selectable flash frequencies. Other applications of the methods may include one or more visual stimulation fields 3 having a left hemi-field zone 16 and a right hemi-field zone 17 with independently selectable flash frequencies. In implementation of the methods, the duration of each stimulus protocol may be selectable. An exemplary duration for each stimulation protocol may be about 10~15 minutes.

In some embodiments, the whole screen visual stimulation field zone 3 or the visual stimulation field zones 14 in each stimulus protocol may be flashed at a flash frequency of at most about 12 Hz (alpha rhythm and lower) to produce inhibition in associated parts of the cerebral cortex of the subject. The whole screen visual stimulation field zone 3 or the visual stimulation field zones 14 in some stimulus protocols may be flashed at least one zone of the visual stimulation field at a flash frequency of greater than about 12 Hz to produce excitation in associated parts of the cerebral cortex of the subject. The visual stimulation field zones 14 in some stimulus protocols may be simultaneously flashed at excitatory (greater than about 12 Hz) and inhibitory (less than about 12 Hz) frequencies to simultaneously excite and inhibit respective parts of the cerebral cortex in the subject.

Each stimulus protocol may be carried out on the subject 30 in daily treatment sessions to modify the brainwave frequencies in the subject 30 and achieve the targeted effect such as maintain the halted or suppressed production of Ab or increase the attention span of the subject 30, for example and without limitation. Each treatment session may include maintaining the reduced EEG frequency of the subject 30 for a selected duration. In some embodiments, the duration may be about 10~15 minutes. In some embodiments, the length of the treatment sessions may be increased to accord with the falling clearance of Ab.

Referring next to FIGS. 3A and 3B of the drawings, a front view of a display screen 2 wish a flashing whole screen visual stimulation field zone 3 is illustrated. The visual stimulation field zone 3 flashes between a dark phase (illustrated in FIG. 3A) and a light phase (illustrated in FIG. 3B) at a selected flash frequency. In some applications, a visual fixation point 20 may appear at substantially the center of the whole screen visual stimulation field zone 3 for enhanced visual focus.

In an exemplary central-peripheral stimulus protocol according to some applications of the methods, the flashing whole screen visual stimulation field zone 3 may stimulate the central and peripheral areas of the visual field of the subject 30 (FIG. 1). Stimulation of the central area of the subject's visual field may entrain the subject's central nervous system in enhancing attention and concentration for focused tasks. Stimulation of the peripheral area of the subject's visual field may entrain the subject's central nervous system in enhancing notice of details and unexpected events. Prior to initiation of the stimulus protocol, the flash frequency and duration of the whole screen visual stimulation field zone 3 may be selected. In some embodiments, the color of the dark phase of the whole screen visual stimulation field zone 3 may be selectable.

Referring next to FIGS. 4A and 4B of the drawings, a front view of a display screen 2 with a flashing left hemi-field zone 16 and a flashing right hemi-field zone 17 is illustrated. The left hemi-field zone 16 flashes between a dark phase (FIG. 4A) and a light phase (FIG. 4B) at a selected flash frequency. Simultaneously, the right hemi-field zone 17 flashes out of phase with the left hemi-field zone 16 between a light phase (FIG. 4A) and a dark phase (FIG. 4B) at the same or at a different flash frequency as the left hemi-field zone 16. In some applications, a visual fixation point 20 may appear at substantially the center of the whole screen visual stimulation field zone 3 between the left hemi-field zone 16 and the right hemi-field zone 17 for enhanced visual focus.

In an exemplary left-right stimulus protocol according to some applications of the methods, the flashing left hemi-field zone 16 and the flashing right hemi-field zone 17 may stimulate the left and right sides, respectively, of the visual field of the subject 30. In a right-handed subject 30, stimulation of the right side of the visual field may entrain the left (dominant) hemisphere of the subject's brain in enhancing comprehension and use of language, rule-based thinking, notice of details and elevated mood. Stimulation of the left side of the visual field may entrain the right (non-dominant) hemisphere of the subject's brain in enhancing 3D perception, face recognition, contexts and intuition. Prior to initiation of the stimulus protocol, the flash frequency and duration of the left hemi-field zone 16 and the right hemi-field zone 17 may be independently selected. In some embodiments, the color of the dark phase of the left hemi-field zone 16 and the right hemi-field zone 17 may be selectable.

Referring next to FIGS. 5A and 5B of the drawings, a front view of a display screen 2 with a flashing upper hemi-field zone 4 and a flashing lower hemi-field zone 10 is illustrated. The upper hemi-field zone 4 flashes between a dark phase (FIG. 5A) and a light phase (FIG. 5B) at a selected flash frequency. Simultaneously, the lower hemi-field zone 10 flashes out of phase with the upper hemi-field zone 4 between a light phase (FIG. 5A) and a dark phase (FIG. 5B) at the same or at a different flash frequency as the upper hemi-field zone 4. In some applications, a visual fixation point 20 may appear at substantially the center of the whole screen visual stimulation field zone 3 between the upper hemi-field zone 4 and the lower hemi-field zone 10 for enhanced visual focus.

In an exemplary upper-lower stimulus protocol according to some applications of the methods, the flashing upper hemi-field zone 4 and the flashing lower hemi-field zone 10 may stimulate the upper and lower areas, respectively, of the visual field of the subject 30. Stimulation of the upper area of the visual field may entrain the corresponding portion of the subject's brain in enhancing recognition of distant objects and faces as well as portions which are involved in memory and motion. Stimulation of the lower area of the visual field may entrain the corresponding portion of the subject's brain in recognizing objects which are sufficiently close to manipulate as well as motor areas of the central nervous system. Prior to initiation of the stimulus protocol, the flash frequency and duration of the upper hemi-field zone 4 and the lower hemi-field zone 10 may be independently selected. In some embodiments, the color of the dark phase of the upper hemi-field zone 4 and the lower hemi-field zone 10 may be selectable.

Referring next to FIGS. 6A and 6B of the drawings, a front view of a display screen 2 with a flashing upper left quadrant zone 5, lower right quadrant zone 12, upper right quadrant zone 6 and lower left quadrant zone 11 is illustrated. The upper left quadrant zone 5 and the lower right quadrant zone 12 may flash in phase with each other, together flashing between the dark phase (FIG. 6A) and the light phase (FIG. 6B) at a selected flash frequency. Likewise, the upper right quadrant zone 6 and the lower left quadrant zone 11 may flash in phase with each other and out of phase with the upper left quadrant zone 5 and the lower right quadrant zone 12, together flashing between the light phase (FIG. 6A) and the dark phase (FIG. 6B) at the same or a different flash frequency. In some applications, a visual fixation point 20 may appear at substantially the center of the whole screen visual stimulation field zone 3 at the junction between the upper left quadrant zone 5, lower right quadrant zone 12, upper right quadrant zone 6 and lower left quadrant zone 11 for enhanced visual focus.

It will be appreciated by those skilled in the art that the entrainment methods for independent stimulation of a visual field in a subject is amenable to a variety of applications and implementations for treatment of brain malfunctions. Referring again to FIG. 2 of the drawings, in some embodiments, the system 1 may be configured to present at least one flashing image of an object or the like in the upper hemi-field zone 4 and the lower hemi-field zone 10, the left hemi-field zone 16 and the right hemi-field zone 17 or the upper left quadrant zone 5, the upper right quadrant zone 6, the lower left quadrant zone 11 and the lower right quadrant zone 12. This option may produce the subjective sensation of a three-dimensional effect to the subject 30. Moreover, in some applications, the visual stimuli imparted by the whole screen visual stimulation field zone 3 and/or the stimulation field zones 14 may be combined with at least one non-visual stimulus including but not limited to an auditory stimulus such as music, binaural beats, neurofeedback, tactile stimuli, kinesthetic stimuli, somatic electrical stimuli, transcranial electrical stimuli and transcranial magnetic stimuli. In applications in which the non-visual stimulus includes music, the system 1 may be programmed to render subtle variations in the visual stimulus to reinforce the musical effect. In some applications, the visual stimuli may be combined with reading material, static pictures and/or video. In some applications, the visual stimuli may be modified dynamically in response to measurements of the subject's physiologic status such as EEG, heat rate, breathing and skin conductance. In some embodiments, the entrainment methods may include presentation of a few lines of text in the center of the whole screen visual stimulation field zone 3. A border around the visual stimulation field may flash at a higher frequency than the whole screen visual stimulation field zone 3. Because children with ADD may lose attention because the task is interrputed by alpha waves, a border which flashes at a higher frequency than the whole screen visual stimulation field zone 3 may help maintain the focus or attention of a child subject.

Figure 7:
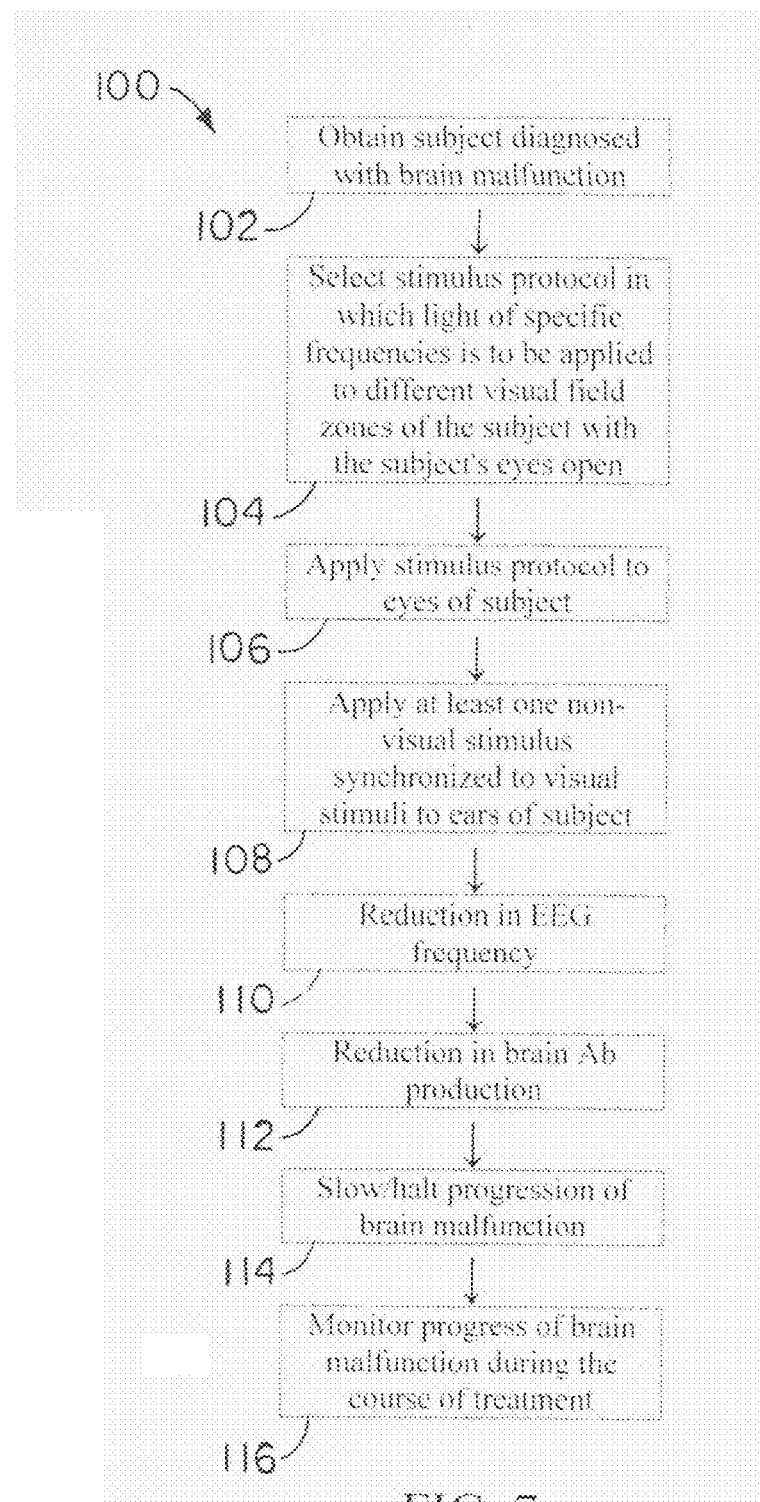
FIG. 7 is a flow diagram of an illustrative embodiment of the methods for independent stimulation of a visual field in a subject in the treatment of brain malfunction related to excessive amyloid protein production accumulation.

Referring next to FIG. 7 in conjunction with FIG. 1 of the drawings, a flow diagram 100 of an illustrative embodiment of the methods for independent stimulation of a visual field in a subject in the treatment of brain malfunction related to excessive amyloid protein production is illustrated. At block 102, a subject which has been diagnosed with a brain malfunction caused or exacerbated by excessive levels of beta amyloid protein (Ab) in the brain is obtained. Non-limiting examples of brain malfunctions which may be caused or exacerbated by excessive levels of Ab and which are amenable to treatment using the methods of the disclosure include Alzheimer's Disease, Down Syndrome and Fragile X Syndrome.

At block 104, a stimulus protocol may be selected. The stimulus protocol may include parameters (visual stimulation field pattern, flash frequency, duration, color, etc.) of the whole screen visual stimulation field zone 3 or visual stimulation field zones 14 which are displayed on the display screen 2. Exemplary flash frequencies which may be selected for the visual stimulation field or the visual stimulation field zones in each stimulus protocol may be generally from about 5 Hz to about 20 Hz. In some embodiments, the stimulus protocol may be selected to reduce or minimize brainwaves having beta (13-30 Hz) and gamma (30+ Hz) EEG frequencies. Brainwave frequencies in the delta (<5 Hz) and/or theta (5-7 Hz) ranges may be selected in some applications to eliminate or at least minimize Ab synthesis. The stimulus protocol may be based on previous data from entrainment sessions of the same or other subjects 30 or from the response of the subject 30 in real time using EEG frequency readings taken from the subject 30.

At block 106, the stimulus protocol may be carried out on the subject 30 in daily treatment sessions to maintain the halted or suppressed production of Ab. The subject 30 may be positioned at a selected distance from the display screen 2 and instructed to visually focus on the whole screen visual stimulation field zone 3 or visual stimulation field zones 14 with both eyes. In some applications, the subject 30 may be positioned at a distance of at least about 6 inches from the whole screen visual stimulation field zone 3 or visual stimulation field zones 14. Each treatment session may include maintaining the reduced EEG frequency of the subject 30 for a selected duration. In some embodiments, the duration may be about 10~15 minutes. In some embodiments, the length of the treatment sessions may be increased to accord with the falling clearance of Ab.

At block 108, at least one non-visual stimulus which may be synchronized to the visual stimuli imparted by the whole screen visual stimulation field zone 3 or the visual stimulation field zones 14 may be applied to the subject. The non-visual stimulus or stimuli may include at least one auditory stimulus, binaural beats, neurofeedback, tactile stimuli, kinesthetic stimuli, somatic electrical stimuli, transcranial electrical stimuli, transcranial magnetic stimuli or any combination thereof.

At block 110, the stimulus protocol results in a reduction in EEG frequency of brainwaves in the subject 30. The reduction in EEG frequency of the brainwaves in the subject 30 reduces Ab production in the brain of the subject 30 (block 112), slowing or halting progression of the brain malfunction (block 114) over time.

At block 116, the progress of the brain malfunction in the subject 30 may be monitored throughout treatment to determine the efficacy of the treatment. Testing for specific chemical changes may be carried out using a blood test, but may require an invasive procedure involving a lumbar puncture with placement of a small drainage tube (cannula) in the spinal canal for several hours. Other methods of monitoring the progress of the brain malfunction in the subject 30 may include periodic fMRI (functional Magnetic Resonance Imaging) of affected areas. The methods of the disclosure may be effective in halting progression of brain malfunctions which are caused or exacerbated by excessive brain levels of amyloid beta protein for several years around the time of clinical onset until a cure (e.g., monoclonal antibody therapy) for the malfunction is found.

Figure 8:
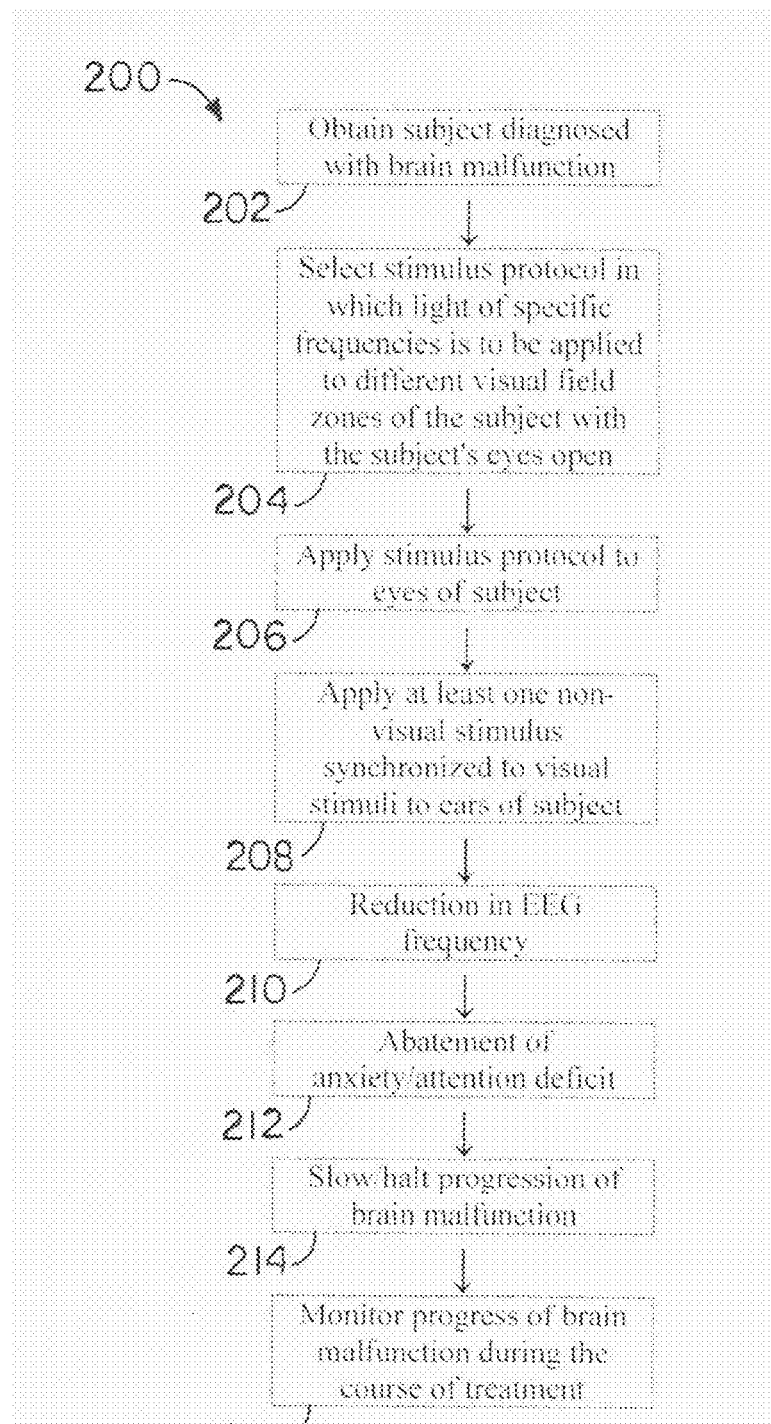
FIG. 8 is a flow diagram of an alternative illustrative embodiment of the methods for independent stimulation of a visual field in a subject in the treatment of anxiety and/or attention deficit disorders.

Referring next to FIG. 8 in conjunction with FIG. 1 of the drawings, a flow diagram 200 of an alternative illustrative embodiment of the methods for independent stimulation of a visual field in a subject in the treatment of anxiety and/or attention deficit disorders is illustrated. At block 202, a subject which has been diagnosed with a brain malfunction such as PTSD (Post Traumatic Stress Disorder) or ADD (Attention Deficit Disorder), for example and without limitation, is obtained.

At block 204, a stimulus protocol may be selected. The stimulus protocol may include parameters (visual stimulation field pattern, flash frequency, duration, color, etc.) of the whole screen visual stimulation field zone 3 or visual stimulation field zones 14 which are displayed on the display screen 2. Exemplary flash frequencies which may be selected for the whole screen visual stimulation field zone or the visual stimulation field zones in each stimulus protocol may be generally from about 5 Hz to about 20 Hz. In some embodiments, the stimulus protocol may be selected to reduce or minimize brainwaves having beta (13-30 Hz) and gamma (30+ Hz) EEG frequencies. Brainwave frequencies in the delta (<5 Hz) and/or theta (5-7 Hz) ranges may be selected in some applications to eliminate or at least minimize Ab synthesis. The stimulus protocol may be baaed on previous data from entrainment sessions of the same or other subjects 30 or from the response of the subject 30 in real time using EEG frequency readings taken from the subject 30.

At block 206, the stimulus protocol may be carried out on the subject 30 in daily treatment sessions to maintain the halted or suppressed production of Ab. The subject 30 may be positioned at a selected distance from the display screen 2 and instructed to visually focus on the visual stimulation field 3 with both eyes. In some applications, the subject 30 may be positioned at a distance of at least about 6 inches from the visual stimulation field 3. Each treatment session may include maintaining the reduced EEG frequency of the subject 30 for at least about 1 hour and typically about 2-4 hours or more. In some embodiments, the length of the treatment sessions may be increased to accord with the falling clearance of Ab.

At block 208, at least one non-visual stimulus which may be synchronized to the visual stimuli imparted by the whole screen visual stimulation field zone 3 or the visual simulation field zones 14 may be applied to the subject. The at least one non-visual stimulus may include at least one auditor, stimulus, binaural beats, neurofeedback, tactile stimuli, kinesthetic stimuli, somatic electrical stimuli transcranial electrical stimuli, transcranial magnetic stimuli or any combination thereof.

At block 210, the stimulus protocol results in a reduction in EEG frequency of brainwaves in the subject 30. The reduction in EEG frequency of the brainwaves in the subject 30 reduces anxiety and/or attention deficit the subject 30 (block 212), slowing or halting progression of the brain malfunction (block 214) over time.

At block 216, the progress of the brain malfunction in the subject 30 may be monitored throughout treatment to determine the efficacy of the treatment. Testing for specific chemical changes may be carried out using a blood test, but may require an invasive procedure involving a lumbar puncture with placement of a small drainage tube (cannula) in the spinal canal for several hours. Other methods of monitoring the progress of the brain malfunction in the subject 30 may include periodic fMRI (functional Magnetic Resonance Imaging) of affected areas. The methods of the disclosure may be effective in halting progression of brain malfunctions which are caused or exacerbated by excessive brain levels of amyloid beta protein for several years around the time of clinical onset until a cure (e.g., monoclonal antibody therapy) for the malfunction is found.

While the illustrative embodiments of the disclosure have been described above, it will be recognized and understood that various modifications can be made to the embodiments and the appended claims are intended to cover all such modifications which may fall within the spirit and scope of the disclosure.

What is claimed is:

1. A method for inducing entrainment in a subject by stimulation of a visual field in said subject, comprising:

presenting a visual stimulation field to a subject for a selected duration, said visual stimulation field including a plurality of zones, each of said plurality of zones having a selected flash frequency, said visual stimulation field being disposed at a distance of at least about six inches from said subject;

fixing said subject's visual attention on a central point on said visual stimulation field for substantially said selected duration; and inducing entrainment in said subject by flashing a plurality of said zones of said visual stimulation field for said selected duration and at the selected flash frequency associated with each of said plurality of zones, wherein each selected flash frequency is different.

2. The method of claim 1 wherein fixing said subject's visual attention comprises instructing said subject to fixate on at least one dot on said visual stimulation field.

3. The method of claim 1 wherein said presenting a visual stimulation field comprises presenting a visual stimulation field on a display screen selected from the group consisting of a computer monitor, LED screen, cathode ray tube, computer tablet display and an optical apparatus adapted to present a focused image on a retina of said subject.

4. The method of claim 1 wherein said flashing a plurality of stimulation field zones comprises flashing a plurality of stimulation field zones selected from the group consisting of a central field zone and a peripheral field zone, an upper hemi-field zone and a lower hemi-field zone, a left hemi-field zone and a right hemi-field zone, a plurality of quadrant zones and a plurality of quadrant subdivision zones.

5. The method of claim 1 wherein said flashing a plurality of zones of said visual stimulation field comprises flashing a plurality of zones of said visual stimulation field having a visual content selected from the group consisting of black, white, solid color, repeated pattern and picture with fine detail.

6. The method of claim 1 wherein said flashing a plurality of zones of said visual stimulation field for a selected duration and at selected flash frequencies comprises flashing a plurality of stimulation field zones with independently selectable flash frequencies for a selected duration and at each selected flash frequency.

7. The method of claim 1 wherein said flashing a plurality of zones of said visual stimulation field at each selected flash frequency comprises flashing at least one zone of said visual stimulation field at a flash frequency of at most about 12 Hz to produce inhibition in associated parts of the cerebral cortex of said subject.

8. The method of claim 1 wherein said flashing a plurality of zones of said visual stimulation field at each selected flash frequency comprises flashing at least one zone of said visual stimulation field at a flash frequency of greater than about 12 Hz to produce excitation in associated parts of the cerebral cortex of said subject.

9. The method of claim 1 wherein said flashing a plurality of zones of said visual stimulation field at each selected flash frequency comprises flashing excitatory and inhibitory frequencies to different ones of a plurality of zones of said visual stimulation field.

10. The method of claim 1 further comprising applying at least one non-visual stimulus selected from the group consisting of auditory stimulus (isochronic tones, binaural beats, music) tactile stimuli, kinesthetic stimuli, somatic electrical stimuli, transcranial electrical stimuli and transcranial magnetic stimuli to said subject.

11. The method of claim 1 further comprising measuring a physiologic variable of said subject and using said physiologic variable to modify said visual stimulation field via neurofeedback.

12. The method of claim 11 wherein measuring a physiologic variable of a subject comprises measuring a physiologic variable selected from the group consisting of EEG, pulse rate, breathing rate and galvanic skin response of said subject.

13. The method of claim 11 wherein using said physiologic variable to modify said visual stimulation field via neurofeedback comprises using said physiologic variable to modify at least one parameter including but not limited to changes in frequency, color and intensity of at least one of said plurality of zones of said visual stimulation field.

14. The method of claim 1 further comprising moving said point on said visual stimulation field while maintaining the plurality of zones of said visual stimulation field in a static relative position, whereby said visual stimulation field produces constant stimulation to zones of the retina of said subject.

15. The method of claim 1 wherein said flashing a plurality of zones of said visual stimulation field for a selected duration and at each selected flash frequency comprises flashing a plurality of zones of said visual stimulation field for a selected duration and at each selected flash frequency to treat a brain malfunction in said subject.

16. The method of claim 15 wherein said flashing a plurality of zones of said visual stimulation field for a selected duration and at each selected flash frequency to treat a brain malfunction in said subject comprises flashing a plurality of zones of said visual stimulation field for a selected duration and at each selected flash frequency to treat a brain malfunction selected from the group consisting of treating post traumatic stress disorder, attention deficit disorder and accumulation of beta amyloid in said subject.

17. A method for inducing entrainment in a subject by stimulation of a visual field in said subject, comprising:
   presenting a visual stimulation field to said subject for a selected duration, said visual stimulation field including a plurality of zones, each of said zones having a selected flash frequency said visual stimulation field being disposed at a distance of at least about six inches from said subject;
   fixing said subject's visual attention on a central point on said visual stimulation field for substantially said selected duration; and
   inducing entrainment in said subject by flashing said plurality of zones of said visual stimulation field for said selected duration and at each selected flash frequency, wherein each selected flash frequency is different.

18. The method of claim 17 further comprising presenting a non-entraining visual image to the visual stimulation field simultaneously with said flashing zones of the visual stimulation field for a selected duration and at each selected flash frequency.

19. The method of claim 18 wherein said presenting a nonentraining visual image to the visual stimulation field comprises presenting an image selected from the group consisting of text, geometric patterns, photographs, paintings and video motion pictures.

* * * * *